United States Patent [19]

Neti et al.

[11] Patent Number: 4,776,942
[45] Date of Patent: Oct. 11, 1988

[54] ELECTROCHEMICAL SENSOR

[75] Inventors: Radhakrishna M. Neti, Brea; David H. Freund, Pomona, both of Calif.

[73] Assignee: Beckman Industrial Corporation, La Habra, Calif.

[21] Appl. No.: 17,719

[22] Filed: Feb. 24, 1987

[51] Int. Cl.⁴ ............................................. G01N 27/30
[52] U.S. Cl. .................................................... 204/415
[58] Field of Search ................. 204/415, 1 P; 128/635

[56] References Cited

U.S. PATENT DOCUMENTS 3,574,078 4/1971 Hynes et al. ........................ 204/415

FOREIGN PATENT DOCUMENTS 3029153 3/1982 Fed. Rep. of Germany ...... 204/415

Primary Examiner—G. L. Kaplan
Attorney, Agent, or Firm—John E. Vanderburgh

[57] ABSTRACT

An improved sensor for dissolved oxygen measurement comprising a body having an electrolyte reservoir and electrolyte contained therein and an opening for communication between the exterior of the body and the reservoir and an anode and cathode concentrically disposed in the body adjacent the opening. A thin polymeric membrane permeable to oxygen and impermeable to the electrolyte seals the opening. The working surfaces of the anode and cathode, that is the surfaces adjacent the membrane, are spaced apart from the membrane to define an electrolyte space between the working surfaces and the membrane. A noble metal screen is disposed on the working surface of the anode. Preferably the screen completely covers the anode working surface and a portion of the screen which would normally overlie the working surface of the cathode is cut away so that the cathode working surface is unobstructed. The noble metal screen over the anode surface results in a substantial retention of electrode stability over a period of time as compared to sensors similarly constructed but which do not include the noble metal screen over the anode working surface.

10 Claims, 2 Drawing Sheets

ELECTROCHEMICAL SENSOR

FIELD OF THE INVENTION

The present invention relates to a sensor capable of detecting a gas in a fluid and more particularly to a sensor capable of measuring the presence of and the quantity of oxygen.

BACKGROUND OF THE INVENTION

One of the electrochemical methods for oxygen determination is the amperometric method. This method is quite rapid, simple in operation and is especially suited for determining either gaseous or dissolved oxygen in liquids. Sensors utilized in the amperometric method of oxygen detection are well known in the art and generally comprise a hollow body defining therein a reservoir for electrolyte and the body is provided with an opening for communication between the exterior and the reservoir. An anode and cathode are disposed within the body for contact with the electrolyte and a thin polymeric membrane, which is impermeable by the electrolyte but which is permeable by oxygen, seals the opening of the body. Means are provided for electrically connecting the electrodes to an electrical potential and to current measuring means. A potential is applied between the anode and the cathode and as sample fluid is brought into contact with the membrane sealing the sensor body, oxygen diffuses through the membrane to contact the cathode in the presence of electrolyte. A current flow results which is linear with the partial pressure of oxygen being sampled. The current is measured and correlated to the amount of oxygen in the sample.

Amperometric oxygen sensors can be said to generally be one of two types. With the first type of sensor, oxygen is reduced as it contacts the cathode thus causing a current flow between anode and cathode. This type of sensor requires a constant $O_2$ flux through the membrane to avoid oxygen depletion within the sensor since $O_2$ is reduced to the hydroxyl group at the cathode and is not regenerated at the anode. This type of sensor is very sensitive to the flow rate of the test fluid and normally requires some means for maintaining a flow of fluid to the sensor. Current flow is directly related to the partial pressure of the oxygen in the test sample. Another type of $O_2$ sensor is the equilibrium type sensor which employs sufficient potential to cause continuous reduction of oxygen from the electrolyte at the cathode and the formation of oxygen at the anode. Once stabilized in operation, an equilibrium condition is set up within the sensor which is disturbed only when the partial pressure of $O_2$ at the exterior surface of the membrane changes, thus disturbing the balance of the equilibrium. Disturbance of equilibrium creates a current flow which is also a direct measure of the partial pressure of oxygen in the sample. Although good results are achieved with both types of sensors, the equilibrium type sensor is preferred because it is independent of flow of oxygen past the membrane surface and does not require control of the sample flow rate or stirring of the sample fluid in the immediate vicinity of the sensor as is normally required with the first type of sensor as described above.

In the equilibrium mode of operation, sensor operation is maximized when the electrodes are concentrically disposed in the sensor body with working surfaces adjacent the inner surface of the membrane. With concentrically disposed electrodes, it is necessary that the ratio of anode surface area to cathode surface area be at least on the order of 85:1. Should the ratio of the anode surface to the cathode surface area be less than about 85:1, the sensor takes an unduly long period of time, on the order of several hours, to stabilize after any step-change in $O_2$ level. Also, long term stability of the sensor is poor even at constant $O_2$ levels with a resulting continuous loss of sensitivity. It has also been found that such sensors exhibit loss of activity over a period of time.

SUMMARY OF THE INVENTION

In accordance with the present invention an improved sensor for dissolved oxygen measurement is provided which comprises a body having an electrolyte reservoir and electrolyte contained therein and an opening for communication between the exterior of the body and the reservoir. An anode and cathode are concentrically disposed in the body adjacent the opening and a thin polymeric membrane permeable to oxygen and impermeable to the electrolyte seals the opening. Means are provided to electrically connect the electrodes to a source of electrical potential and current measuring means. The working surfaces of the anode and cathode, that is the surfaces adjacent the membrane, are spaced apart from the membrane to define an electrolyte space between the working surfaces and the membrane. A noble metal screen is disposed on the working surface of the anode. In the preferred embodiment of the invention the screen completely covers the anode working surface and a portion of the screen which would normally overlie the working surface of the cathode is cut away so that the cathode working surface is unobstructed.

Although the reasons are not clearly understood, the use of the noble metal screen over the anode surface results in a substantial retention of electrode stability over a period of time as compared to sensors similarly constructed but which do not include the noble metal screen over the anode working surface.

In a highly preferred embodiment of the sensor of the present invention, the cathode is comprised of rhodium metal and the anode and the noble metal screen are comprised of platinized platinum.

BRIEF DESCRIPTION OF THE DRAWINGS

The invention will be more fully understood from the following detailed description taken in conjunction with the drawings of which.

FIG. is a side elevation, partially in section, of an oxygen sensor constructed in accordance with the invention.

DESCRIPTION OF THE INVENTION

Figure 1:
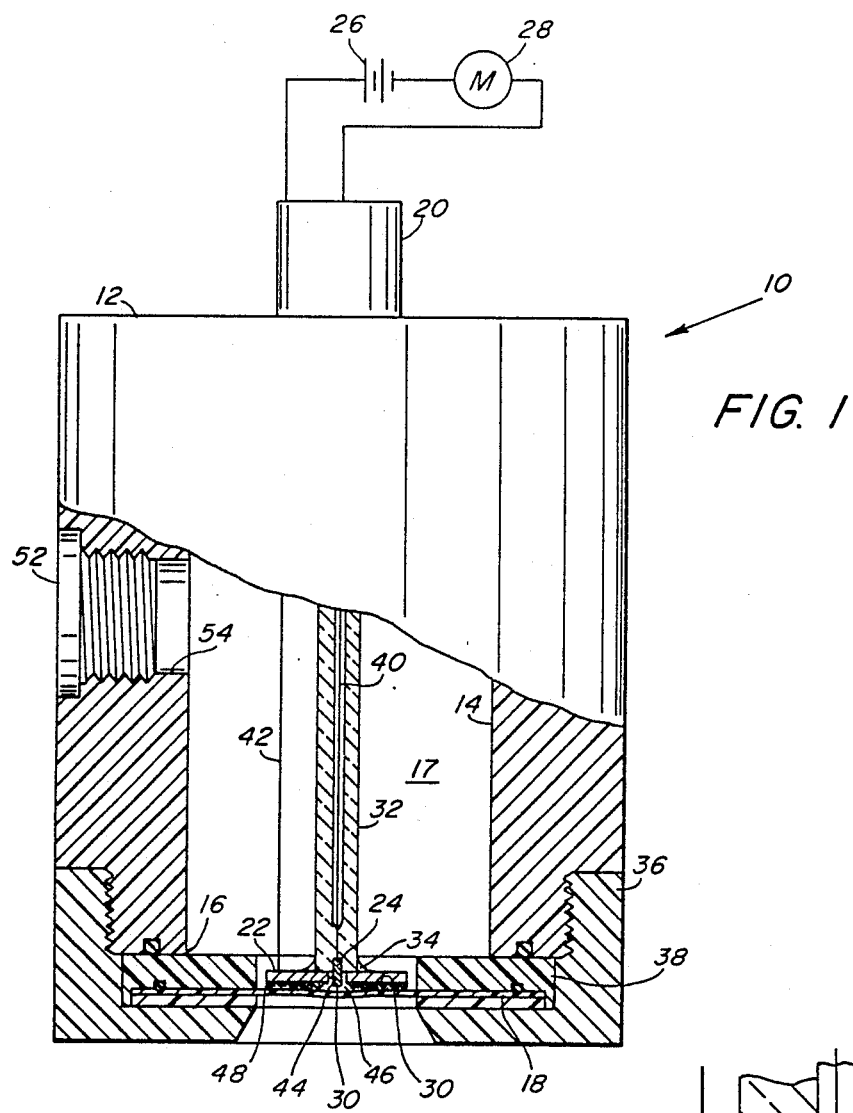
Figure 3:
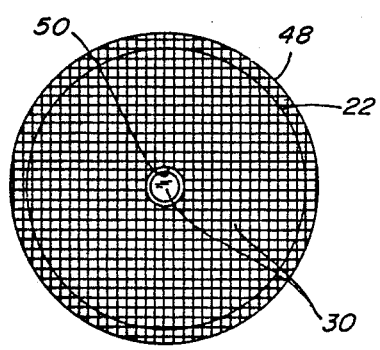
FIG. 3 is an end view of the sensor as illustrated in FIG. 2.

Referring to FIG. 1, the preferred embodiment of the present invention is shown as a sensor for oxygen, shown generally as 10, comprising a body 12 having an interior defining a reservoir 14 which contains an electrolyte 17 therein. The body 12 has an opening at 16 for communication between the reservoir 14 and the exterior of the body. An anode 22 and a cathode 24 are concentrically disposed in the body 12 adjacent the opening 16. A thin polymeric membrane 18 seals the opening 16. The membrane 18 is preferably formed from either fluoroethylenepropylene or tetralfuoroethylene which is permeable to oxygen but which is electrolyte impermeable. Terminal means 20 are provided to connect the electrodes electrically to a source of potential 26 and current measuring means 28. The anode 22 and cathode 24 are supported in the reservoir 14 by a glass tube 32. The cathode 24 is fused in one end of the glass tube 32. The anode 22, which is generally disc shaped, is provided with a central aperture 44 in which the cathode 24 is concentrically disposed. The anode 22 is carried by the end of the glass tube 32 and is affixed thereto by an adhesive material 34 which is resistant to the electrolyte, such as for example epoxy adhesives. The anode 22 and the cathode 24 are connected to the terminal means 20 by means of cathode lead 40 and anode lead 42. The membrane 18 is held in place over the body opening 16 by a threaded annular cap 36 which cooperates with a ring 38 to clamp the membrane in position.

When properly positioned in the body 12 the anode 22 and the cathode 24 are located adjacent the opening 16 with the lower working surfaces 30 adjacent to the membrane 18 but slightly spaced therefrom to define an electrolyte space 46 between the working surfaces and the membrane. A threaded plug 52 seals a corresponding threaded opening 54 in the side of the sensor body 12 for adding or removing electrolyte from the reservoir 14.

In accordance with the invention, a noble metal screen 48 is disposed on the working surface 30 of the anode 22. The screen 48 is provided with an opening 50 which is aligned with the working surface 30 of the cathode 24 so that the cathode working surface is fully exposed to electrolyte in the electrolyte space 46. The screen, however, covers the entire working surface 30 of the anode 22.

The anode 22 is comprised of a noble metal, preferably platinum over which is deposited a layer of platinum black. The cathode 24 also comprises a noble metal although in the case of oxygen sensors of the type to which the present invention relates, it is highly preferred that the cathode be composed of rhodium as it is highly resistant to $CO_2$ interference. The ratio of surface area of the anode to the surface area of the cathode must be at least 85 to 1 and may go as high as 100 to 1. It is highly preferred to platinize or deposit platinum black on the working surface of the anode 22 since the layer of platinum black apparently increases the surface area of the anode which improves the aforementioned ratio without decreasing the size of the cathode unnecessarily or without increasing the dimensions of the sensor in order to achieve the desired anode to cathode ratio.

The noble metal screen is preferably comprised of the same material as the anode 22 and is also preferably coated with platinum black. The screen 48 is affixed on the working surface 30 of the anode 22 by suitable means such as spot welding and in the preferred embodiment the screen is affixed to the working surface of the anode prior to applying the platinum black so that the screen and the working surface are platinized at the same time. The screen may range between 50 mesh to 1000 mesh. Good results are achieved with a wire screen of 100 mesh US Sieve Series with a wire diameter of about 0.003 inches. The 100 mesh screen size provides an opening on the order of 0.007 inches which is sufficient to allow for a good buildup of platinum black on the screen and on the working surface 30 of the anode 22. Although the finer mesh sizes produce good results if the screen 48 is platinized separately from the anode 22, the openings of the finer mesh screens tend to be filled in thus reducing the surface area of the anode working surface when the screen and anode are assembled and then platinized. On the other hand, the mesh sizes coarser than about 50 mesh US Standard Sieve Series do not provide the optimum increase in working surface area provided by the finer mesh sizes, i.e., 50 to 1000 mesh.

In a highly preferred embodiment of the invention the noble metal screen 48 is subjected to a compression operation prior to assembly on the working surface 30 of the anode 22. It will be understood that the screen 48 in its position on the working surface 30 of the anode 22 also serves as a spacer between the membrane 18 and the cathode 24 and although it is not fully understood, it is believed that the compression operation minimizes the electrolyte space 46 between the cathode and the membrane thus producing a quicker response in the sensor. However, it will be understood that the aforementioned compression step is not critical and may be eliminated in the assembly of the sensor in accordance with the present invention.

Figure 2:
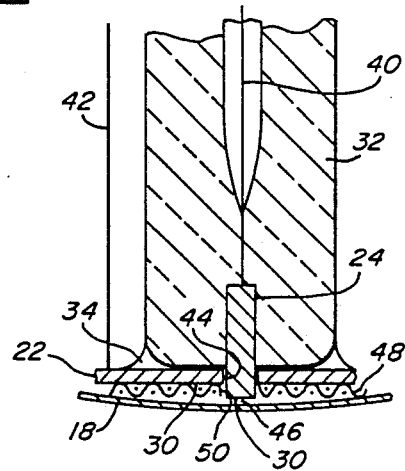
FIG. 2 is a sectional view in enlarged scale of a portion of the sensor of FIG. 1.

By way of example, an electrode sensor was constructed in accordance with the description and illustration FIGS. 1 and 2 without a noble metal screen on the working surface 30 of the anode 22. The cathode was a 0.040 inch rhodium wire fused in a glass tube and the anode was a 0.25 inch platinum disc provided with a 0.05 inch center cutout. The platinum disc was bounded on the end of the glass tube and the cathode was concentrically disposed in the opening of the anode. The anode was provided in the opening of platinum black on its working surface 30. The electrodes were assembled in a sensor body 12 provided with an opening 16 which was sealed by a 0.02 fluoroethylenepropylene membrane. The electrolyte was a two percent KOH solution.

The sensor so constructed was installed in an environmental chamber which contained ordinary atmosphere and cycled through a series of temperature steps. The first temperature step began at 4° C. for a minimum period of 4 to 5 hours. At the completion of this period, the temperature was increased to 25° C. for a minimum period of 4 hours and then stepped up to 44° C. for a minimum of 4 hours. At the completion of the 44° C. temperature period the temperature was reduced to 4° C. and the cycle repeated. The sensor was exposed to the temperature cycles and the signal output recorded for four complete cycles.

Figure 4:
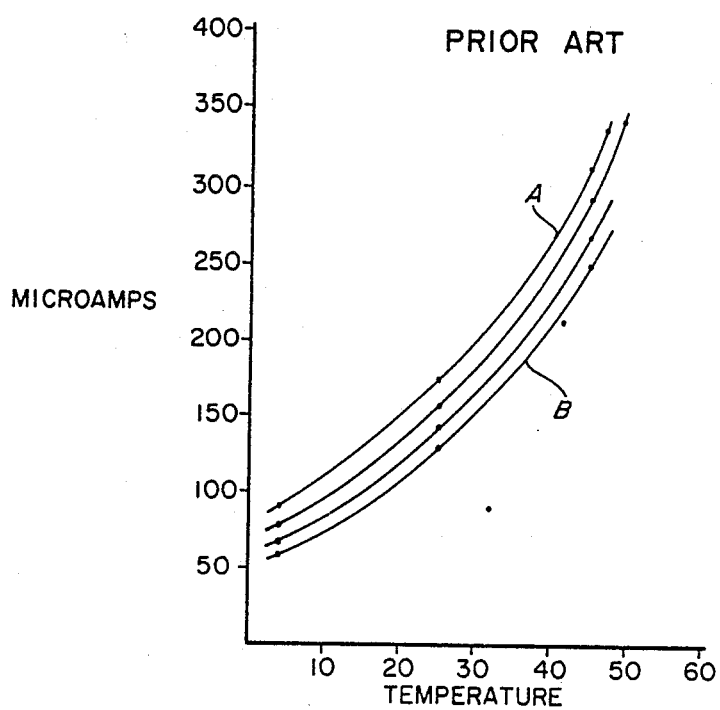
FIG. 4 is a plot of sensor output in microamps versus temperature plotted over a period of time for an oxygen sensor constructed in accordance with the prior art.

The results are plotted in FIG. 4 with line A representing the signal output at the various temperatures for the sensor during the first cycle and line B representing the signal output during the fourth or final cycle. As can be seen from FIG. 4 the signal output of the sensor increases with increasing temperature. More importantly, however, it will be seen that the signal strength regardless of temperature is substantially less by the completion of the fourth cycle. The test represents four weeks of usage of the sensor. From FIG. 4 it can be seen that over the test cycle the sensor exhibits a substantial loss in signal strength. In fact the loss of signal strength is greater than the loss allowed by product specifications and the sensor is unacceptable for use. Accordingly, the sensor must be replaced or a new platinum black surface applied to the working surface of the electrodes.

At the completion of the four cycles the same sensor was retrieved from the environmental chamber, disassembled and a platinized platinum screen, 100 mesh, was affixed on the working surface of the anode. The sensor was reassembled using the same type of membrane and electrolyte and placed back in the environmental chamber and subjected to five cycles of temperature which extended over 5 weeks of continuous use.

Figure 5:
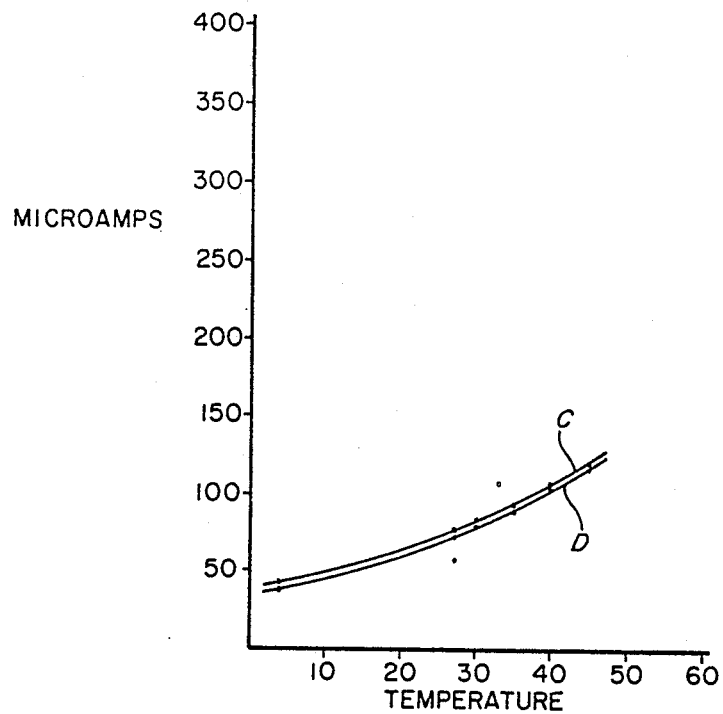
FIG. 5 is a plot of sensor output in microamps versus temperature taken at two time periods for an oxygen sensor constructed in accordance with the invention.

The results are illustrated in FIG. 5. As can be seen there is only slight decrease in signal strength over the temperature ranges between the first cycle, line C, and the fifth cycle, line D. The decrease in signal strength is within accpetable specified limits even after 5 weeks of continuous use.

While various embodiments and modifications of the invention have been described in the foregoing description and illustrated in the drawings, it will be understood that minor changes may be made in details of construction as well as in the combination and arrangement of parts without departure from the spirit and scope of the invention as claimed. For example, the anode 22 may comprise a sintered metal. In addition, good results are achieved using a tube type anode rather than the disc shaped anode as illustrated. The choice of electrolyte will be apparent to those skilled in the art and the electrolyte may be buffered or non-buffered as set forth in the examples.

Having described the invention, we claim:

1. In a sensor for dissolved oxygen comprising a body having an electrolyte reservoir therein, an opening in said body for communication between the exterior of said body and said reservoir, a thin polymeric membrane permeable to oxygen and impermeable to electrolyte sealing said opening, terminal means electrically connected to a source of electrical potential and current measuring means, electrodes defining an anode and a cathode concentrically disposed in said body, said electrodes having working surfaces adjacent said membrane and spaced apart therefrom to define an electrolyte space therebetween, the improvement comprising;

a noble metal screen disposed on the working surface of said anode whereby loss of electrode activity is minimized and a high ratio of anode to cathode area is maintained over a period of time and temperature range.

2. The sensor for dissolved oxygen of claim 1 wherein said noble metal screen is platinum and allows thereof.

3. The oxygen sensor of claim 1 wherein said noble metal screen is 50 mesh to 1000 mesh.

4. The oxygen sensor of claim 1 wherein said cathode is rhodium.

5. The oxygen sensor of claim 1 wherein said noble metal screen comprises an outer layer of platinum black.

6. The oxygen sensor of claim 1 wherein said anode to cathode ratio is at least about 85:1.

7. The oxygen sensor of claim 1 wherein said noble metal screen is affixed to the working surface of said anode thereby to maintain its position thereon.

8. The oxygen sensor of claim 7 wherein said noble metal screen is spot welded to said anode working surface.

9. The oxygen sensor of claim 1 wherein said noble metal screen is compressed thereby to minimize the electrolyte space between said cathode and said membrane.

10. The oxygen sensor of claim 1 wherein said noble metal screen overlies essentially the entire area of the working surface of said anode.

* * * * *

UNITED STATES PATENT AND TRADEMARK OFFICE
CERTIFICATE OF CORRECTION

PATENT NO. : 4,776,942
DATED : October 11, 1988
INVENTOR(S) : Radhakrishna M. Neti et al It is certified that error appears in the above-identified patent and that said Letters Patent is hereby corrected as shown below:

In claim 2, column 6, line 16 change "allows" to --alloys--

Signed and Sealed this

Twenty-eighth Day of March, 1989

*Attest:*

DONALD J. QUIGG

*Attesting Officer*   *Commissioner of Patents and Trademarks*